United States Patent
Jones et al.

(10) Patent No.: US 7,955,371 B2
(45) Date of Patent: Jun. 7, 2011

(54) SYSTEM AND METHOD FOR STENT DEPLOYMENT AND INFUSION OF A THERAPEUTIC AGENT INTO TISSUE ADJACENT TO THE STENT ENDS

(75) Inventors: Ryan A Jones, Santa Rosa, CA (US); John D Kantor, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 369 days.

(21) Appl. No.: 10/921,680

(22) Filed: Aug. 18, 2004

(65) Prior Publication Data
US 2005/0267561 A1    Dec. 1, 2005

Related U.S. Application Data

(60) Provisional application No. 60/570,221, filed on May 12, 2004.

(51) Int. Cl.
*A61F 2/84* (2006.01)
(52) U.S. Cl. ............................ 623/1.11; 604/264
(58) Field of Classification Search .............. 623/1.11, 623/1.46; 606/194; 604/104–106, 108, 264, 604/96.01, 97.01, 102.01–102.03, 117
See application file for complete search history.

(56) References Cited

U.S. PATENT DOCUMENTS

| | | | |
|---|---|---|---|
| 4,739,762 A | 4/1988 | Palmaz | |
| 5,133,732 A | 7/1992 | Wiktor | |
| 5,292,331 A | 3/1994 | Boneau | |
| 5,421,955 A | 6/1995 | Lau et al. | |
| 5,571,086 A * | 11/1996 | Kaplan et al. | 604/96.01 |
| 5,681,281 A * | 10/1997 | Vigil et al. | 604/103.01 |
| 5,788,979 A * | 8/1998 | Alt et al. | 424/426 |
| 6,090,127 A | 7/2000 | Globerman | |
| 6,200,325 B1 * | 3/2001 | Durcan et al. | 606/108 |
| 6,283,951 B1 | 9/2001 | Flaherty et al. | |
| 6,302,870 B1 * | 10/2001 | Jacobsen et al. | 604/272 |
| 6,383,212 B2 * | 5/2002 | Durcan et al. | 623/1.11 |
| 6,547,767 B1 * | 4/2003 | Moein | 604/264 |
| 2001/0004696 A1 * | 6/2001 | Roberts et al. | 606/108 |
| 2003/0023301 A1 * | 1/2003 | Cox et al. | 623/1.15 |
| 2003/0040712 A1 * | 2/2003 | Ray et al. | 604/173 |
| 2003/0055446 A1 | 3/2003 | Seward et al. | |
| 2004/0210188 A1 * | 10/2004 | Glines et al. | 604/68 |

* cited by examiner

*Primary Examiner* — Ryan J Severson

(57) ABSTRACT

The invention provides a system and method for deploying a stent and infusing a therapeutic agent into tissue adjacent to the ends of the stent. The system comprises a catheter, an inflatable balloon, a stent, and a plurality of infusion elements. The catheter has an inflation lumen and at least one therapeutic agent delivery lumen. The balloon is disposed on the catheter and is in fluid communication with the inflation lumen. The stent is disposed on the balloon. The infusion elements are positioned adjacent to distal and proximal ends of the stent and are in fluid communication with at least one therapeutic agent delivery lumen. The infusion elements are inserted into a wall of a target region of a vessel responsive to inflation of the balloon. Further inflation of the balloon deploys the stent within the target region.

18 Claims, 4 Drawing Sheets

SYSTEM AND METHOD FOR STENT DEPLOYMENT AND INFUSION OF A THERAPEUTIC AGENT INTO TISSUE ADJACENT TO THE STENT ENDS

RELATED APPLICATIONS

This application claims the benefit of U.S. Provisional Patent Application No. 60/570,221 filed May 12, 2004.

TECHNICAL FIELD

This invention relates generally to treatment of vascular conditions. More specifically, the invention relates to a system and method for deploying a stent and infusing a therapeutic agent into tissue adjacent to the ends of the stent.

BACKGROUND OF THE INVENTION

Heart disease, specifically coronary artery disease, is a major cause of death, disability, and healthcare expense in the United States and other industrialized countries. A number of methods and devices for treating coronary artery disease have been developed, some of which are specifically designed to treat the complications resulting from atherosclerosis and other forms of coronary arterial narrowing.

One method for treating such vascular conditions is percutaneous transluminal coronary angioplasty (PTCA). During PTCA, a balloon catheter device is inflated to dilate a stenotic blood vessel. The stenosis may be the result of a lesion such as a plaque or thrombus. When inflated, the pressurized balloon exerts a compressive force on the lesion, thereby increasing the inner diameter of the affected vessel. The increased interior vessel diameter facilitates improved blood flow.

However, soon after the procedure, a significant proportion of treated vessels restenose. Various methods have been developed to prevent or inhibit this restenosis. One method is to provide a physical support in the form of a stent to maintain the increased interior diameter of the vessel lumen.

Stents are generally cylindrical shaped devices that are radially expandable to hold open a segment of a vessel or other anatomical lumen after implantation into the body lumen. Various types of stents are in use, including expandable and self-expanding stents. Expandable stents generally are conveyed to the area to be treated on balloon catheters or other expandable devices. For insertion, the stent is positioned in a compressed configuration along the delivery device, for example crimped onto a balloon that is folded or otherwise wrapped about a guide wire that is part of the delivery device. After the stent is positioned across the lesion, it is expanded by the delivery device, causing the diameter to expand. For a self-expanding stent, commonly a sheath is retracted, allowing expansion of the stent.

The stent acts as a scaffold to support the lumen in an open position. Configurations of stents include a cylindrical tube defined by a mesh, interconnected stents, or like segments. Exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz, and U.S. Pat. No. 5,421,955 to Lau.

Stents have been used with coatings to deliver drugs or other therapeutic agents at the site of the stent to assist in preventing inflammation, infection, thrombosis, and proliferation of cell growth that can occlude the vessel lumen. However, the coated stent can deliver drugs to only those portions of the vessel in contact with the stent. Because restenosis is often a greater problem in tissue adjacent to the ends of a stent than it is elsewhere along the stent, drug delivery using the stent alone may not be fully effective.

Vascular delivery of drugs and other agents intended to inhibit restenosis has also been accomplished using devices that inject or otherwise infuse the agents into the treated portion of the vessel before, during, or after performing PTCA. Unlike coated stents, these devices deliver the anti-restenosis agents without additionally providing physical support for the treated vessel.

One such device is disclosed in U.S. patent application Publication No. 2003/0055446 to Seward and Pisano. This device includes an actuator joined to a distal end of a catheter. The actuator has an expandable section designed to deploy a needle. When the expandable section is in an unactuated, furled condition, the needle is enclosed within the folds of the expandable section, preventing the needle from injuring the vessel walls while the catheter is being introduced into the target area of a vessel. Fluid connections are provided to supply a therapeutic or diagnostic agent to the needle and to provide an activating fluid to the actuator. When actuated, the expandable section unfurls and expands, thrusting the needle outward, penetrating the vessel wall and delivering the agent. When the activating fluid is removed, the expandable section returns to a furled state with the needle again enclosed within the folds of the expandable section for removal of the catheter from the vessel.

Another device for vascular delivery of therapeutic agents is disclosed in U.S. Pat. No. 5,681,281 to Vigil and Barath. In one embodiment, the device includes an inflatable balloon mounted on a catheter. A tubular sheath surrounds a substantial portion of the inflatable balloon, and a plurality of injectors is mounted on the sleeve. In another embodiment, a plurality of tubular fluid passageways is mounted on the balloon, extending longitudinally across the balloon, and a plurality of injectors is mounted on each fluid passageway. In both embodiments, inflation of the balloon embeds the injectors in a vessel wall, and a medication is delivered through the injectors into the vessel wall.

Still another device for delivering drugs to a vessel is disclosed in U.S. Pat. No. 6,283,951 to Flaherty et al. The device includes a catheter, an orientation element in a predetermined relationship with the periphery of the catheter, a drug delivery element, and in some embodiments a puncturing element and/or an imaging element. In one embodiment, the drug delivery element is an osmotic surface on the catheter. In another embodiment, a puncturing element, for example a needle, is deployed through an opening in a distal portion of the catheter. The drug delivery element, in this example a lumen within the needle, delivers a drug to the tissue. The drug delivery element may include electrodes that, when current is passed between the electrodes, direct a fluid ionophoretically.

Thus, coated stents support the lumen of a vessel in an open position following PTCA but may be limited in their ability to deliver an anti-restenosis agent to the wall of the treated vessel. Injection devices, on the other hand, offer flexibility in delivery of an anti-restenosis agent do not provide scaffolding to maintain the increase in the interior diameter of a vessel lumen that has been achieved by performing PTCA. Therefore, it would be desirable to have a system and method for treating a vascular condition that overcome the aforementioned and other disadvantages.

SUMMARY OF THE INVENTION

One aspect of the present invention is a system for treating a vascular condition comprising a catheter, an inflatable balloon, a stent, and a plurality of infusion elements. The catheter has an inflation lumen and at least one therapeutic agent delivery lumen. The balloon is disposed on the catheter and is in fluid communication with the inflation lumen. The stent is disposed on the balloon. The infusion elements are positioned adjacent to distal and proximal ends of the stent and are in fluid communication with at least one therapeutic agent delivery lumen.

Another aspect of the present invention is a method of treating a vascular condition. A system is provided comprising a catheter having an inflation lumen and at least one therapeutic agent delivery lumen, a balloon disposed on the catheter, a stent disposed on the balloon, and a plurality of therapeutic agent infusion elements positioned adjacent to proximal and distal ends of the stent. The system is introduced into a vessel containing a target region identified for treatment and guided to a position adjacent to the target region. The balloon is inflated. The infusion elements are inserted into a wall of the vessel responsive to inflation of the balloon, and at least one therapeutic agent is delivered into the wall of the vessel via the infusion elements. The stent is deployed responsive to inflation of the balloon. The balloon is deflated, withdrawing the infusion elements from the wall of the target region. The system is then removed from the vessel.

The aforementioned and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE PRESENTLY PREFERRED EMBODIMENTS

Figure 1A:
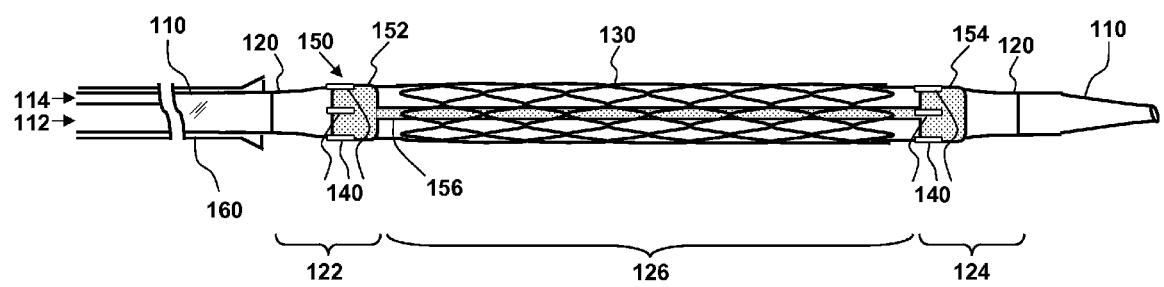
FIG. 1A is an illustration of one embodiment of a system for treating a vascular condition, in accordance with the present invention, shown prior to inflating the balloon.
Figure 1B:
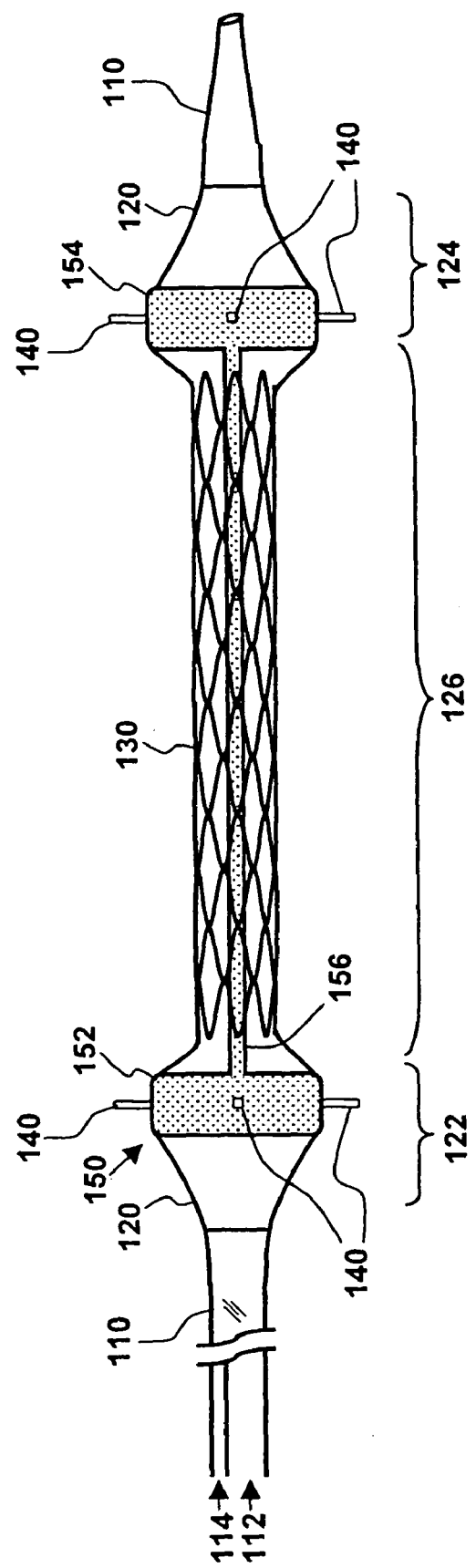
FIG. 1B shows the system of FIG. 1A with proximal and distal end portions of the balloon inflated and infusion elements deployed.
Figure 1C:
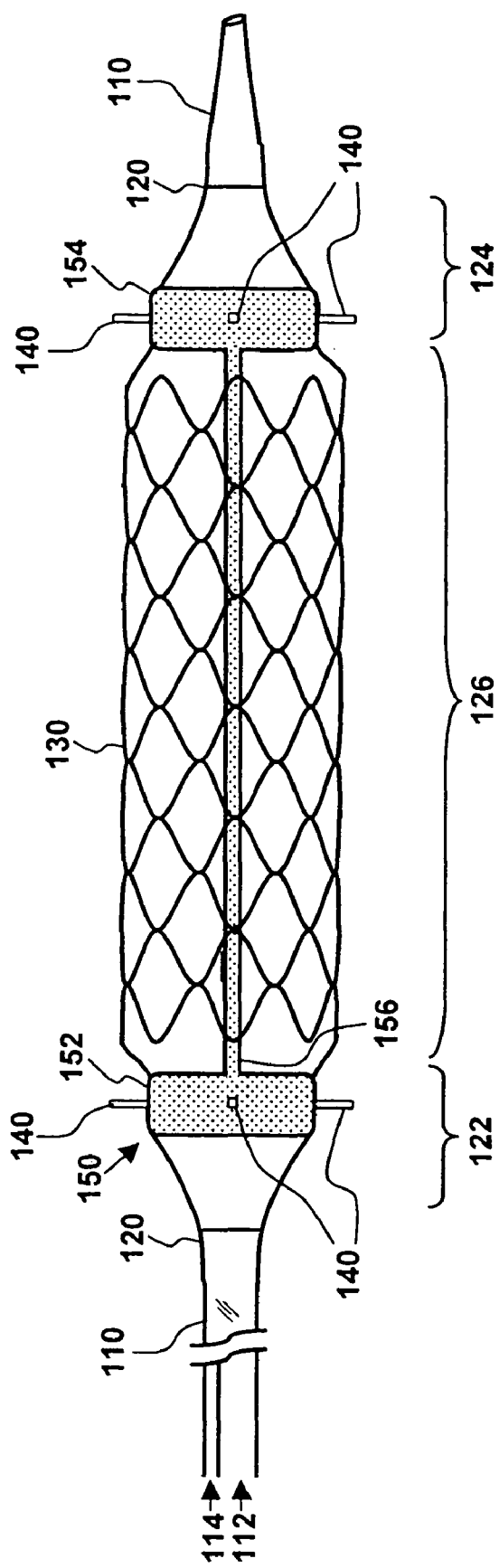
FIG. 1C shows the system of FIGS. 1A and 1B with the center portion of the balloon inflated and the stent deployed.

One aspect of the present invention is a system for treating a vascular condition. One embodiment of the system, in accordance with the present invention, is illustrated in FIGS. 1A through 1C. The system comprises a catheter 110, a balloon 120, a stent 130, and infusion elements 140 mounted on a manifold 150. A retractable sheath 160, is also included in the present embodiment. Catheter 110 has an inflation lumen 112 and a therapeutic agent delivery lumen 114. Balloon 120 comprises a proximal end portion 122, a distal end portion 124, and a center portion 126. Manifold 150 comprises a proximal section 152, a distal section 154, and a linking section 156.

Catheter 110 may be any catheter known in the art that is appropriate for delivering a stent to a treatment site within a vessel, for example a percutaneous transluminal coronary angioplasty (PTCA) balloon catheter. Catheter 110 includes inflation lumen 112 for inflating balloon 120 and therapeutic agent delivery lumen 114 for delivering a therapeutic agent to infusion elements 140 via manifold 150. While a single therapeutic agent delivery lumen is shown, one skilled in the art will appreciate that catheter 110 may include multiple delivery lumens for delivering multiple therapeutic agents.

Balloon 120 may be made of a suitable material such as polyethylene, polyethylene terephthalate (PET), or from nylon or the like. In the present embodiment, balloon 120 is a stepped balloon, meaning that the inflation diameter of balloon 120 steps up from proximal end portion 122 to center portion 126 and then steps down from center portion 126 to distal end portion 124. This can be seen best in FIG. 1C, where center portion 126 of balloon 120 is shown to have a greater inflation diameter than that of proximal and distal end portions 122 and 124. In this example, center portion 126 is about 10 millimeters in length, with each of proximal and distal end portions 122 and 124 being about 2 millimeters in length. Center portion 126 is designed to achieve an inflation diameter at least as great as the inner diameter of the vessel to be treated, with the inflation diameters of proximal and distal end portions 122 and 124 being adequate to insert infusion elements 140 into the wall of the vessel. In the exemplary embodiment illustrated in FIGS. 1A-1C, the axial lengths of the manifold proximal section 152 and the manifold distal section 154 are less than the axial length of the proximal end portion 122 and the distal end portion 124, respectively.

In the present embodiment, manifold 150 is formed from a suitable biocompatible polymer such as polytetrafluoroethylene (PTFE), expanded polytetrafluoroethylene (ePTFE), spun polyester, or Dacron. Manifold 150 is disposed on balloon 120 and is in fluid communication with therapeutic agent delivery lumen 114. Manifold proximal section 152 is disposed on balloon proximal end portion 122, manifold distal section 154 is disposed on balloon distal end portion 124, and manifold linking section 156 is disposed on balloon center portion 126. Proximal and distal manifold sections 152 and 154 extend around the circumference of the balloon portions on which they are disposed. Manifold linking section 156 extends longitudinally across balloon center portion 126 and provides fluid communication between the proximal and distal sections of the manifold. In the present embodiment, proximal section 152 is in fluid communication with therapeutic agent delivery lumen 114, and distal section 154 receives the therapeutic agent or agents via linking section 156. Alternatively, distal section 154 may be in fluid communication with therapeutic agent delivery lumen 114, and proximal section 152 may receive the therapeutic agent or agents via linking section 156.

A portion of the infusion elements are mounted on manifold proximal section 152, and the remaining infusion elements are mounted on manifold distal section 154. The number of infusion elements may be varied to achieve maximum distribution of the therapeutic agent or agents within the vessel wall. In the present embodiment, infusion elements 140 are hollow needles made of stainless steel or another appropriate biocompatible material. The needles are attached to the manifold by, for example, bonding the needles to the manifold or by inserting the needles into polymeric tubes and bonding the tubes to the manifold. The lengths of the needles are dependent on the inflation diameters of balloon 120, with the combined diameter of the needles and the balloon end portion on which they are mounted being about five to ten percent greater than the inflation diameter of balloon center portion 126.

In an alternative embodiment, the system may include two separate manifolds, one extending around the circumference of the proximal end portion of the balloon and the other extending around the distal end portion of the balloon. A portion of the infusion elements are mounted on one manifold, with the remaining infusion elements mounted on the other manifold. In this embodiment, the two manifolds are not linked but are each separately connected to at least one therapeutic agent delivery lumen. The two manifolds may be in fluid communication with the same therapeutic agent delivery lumen or lumens or with different lumens.

In the present embodiment, stent 130 is disposed on balloon 120 with manifold linking section 156 sandwiched between the balloon and the stent. Stent 130 may be made of a wide variety of medical implantable materials, including, but not limited to, stainless steel, nitinol, tantalum, ceramic, nickel, titanium, aluminum, polymeric materials, MP35N, stainless steel, titanium ASTM F63-83 Grade 1, niobium, high carat gold K 19-22, and combinations thereof.

A therapeutic coating (not shown) is disposed on at least a portion of the stent. The therapeutic coating may include, for example, an antineoplastic agent, an antiproliferative agent, an antibiotic, an antithrombogenic agent, an anticoagulant, an antiplatelet agent, an anti-inflammatory agent, combinations of the above, and the like.

The profile of balloon 120, stent 130, and manifold 150 with its attached infusion elements 140 is shown minimized for delivery of the system into a vessel in FIG. 1A. In the present embodiment, a sheath 160 covers the infusion elements while the system is being introduced into the target area of the vessel, thereby preventing the infusion elements from injuring the vessel walls. In an alternative embodiment, either or both of the manifold and the balloon may be folded such that the infusion elements are held within the folds of the uninflated balloon and/or manifold during delivery of the system to a target region within a vessel. The vessel is thereby shielded from the infusion elements, eliminating the need for a sheath.

As seen in FIG. 1B, proximal and distal edge portions 122 and 124 of balloon 120 inflate at a first inflation pressure, bringing the infusion elements up roughly perpendicular to the vessel wall and thrusting them into the wall for delivery of one or more therapeutic agents. Stent 130 constrains balloon center portion 126 from inflating until a second, greater inflation pressure is delivered.

FIG. 1C shows the system after this second inflation pressure has been delivered to balloon 120. Balloon center section 126 is expanded, and stent 130 is deployed against the vessel walls (not shown). In an alternative embodiment, a single inflation pressure may inflate all portions of the balloon, delivering the stent at approximately the same time the infusion elements are thrust into the wall of the vessel.

Once stent 130 has been deployed, balloon 120 is deflated, and the sheath is returned to a position covering the infusion elements. The sheath may be tapered, with the larger opening of the sheath being adjacent to the balloon when the sheath is retracted. This larger opening increases the ease with which the sheath can be drawn back over the balloon, manifold(s), and infusion elements. One skilled in the art will recognize that a wide range of shapes are possible for the sheath, and more than one sheath may be used to cover the infusion elements. In an alternative embodiment, the need for a sheath may be eliminated by moving the infusion elements back inside the folds of the deflated balloon and/or manifold in response to deflation of the balloon, thereby enclosing the infusion elements and preventing trauma to the vessel during removal of the catheter from the vessel.

Figure 2:
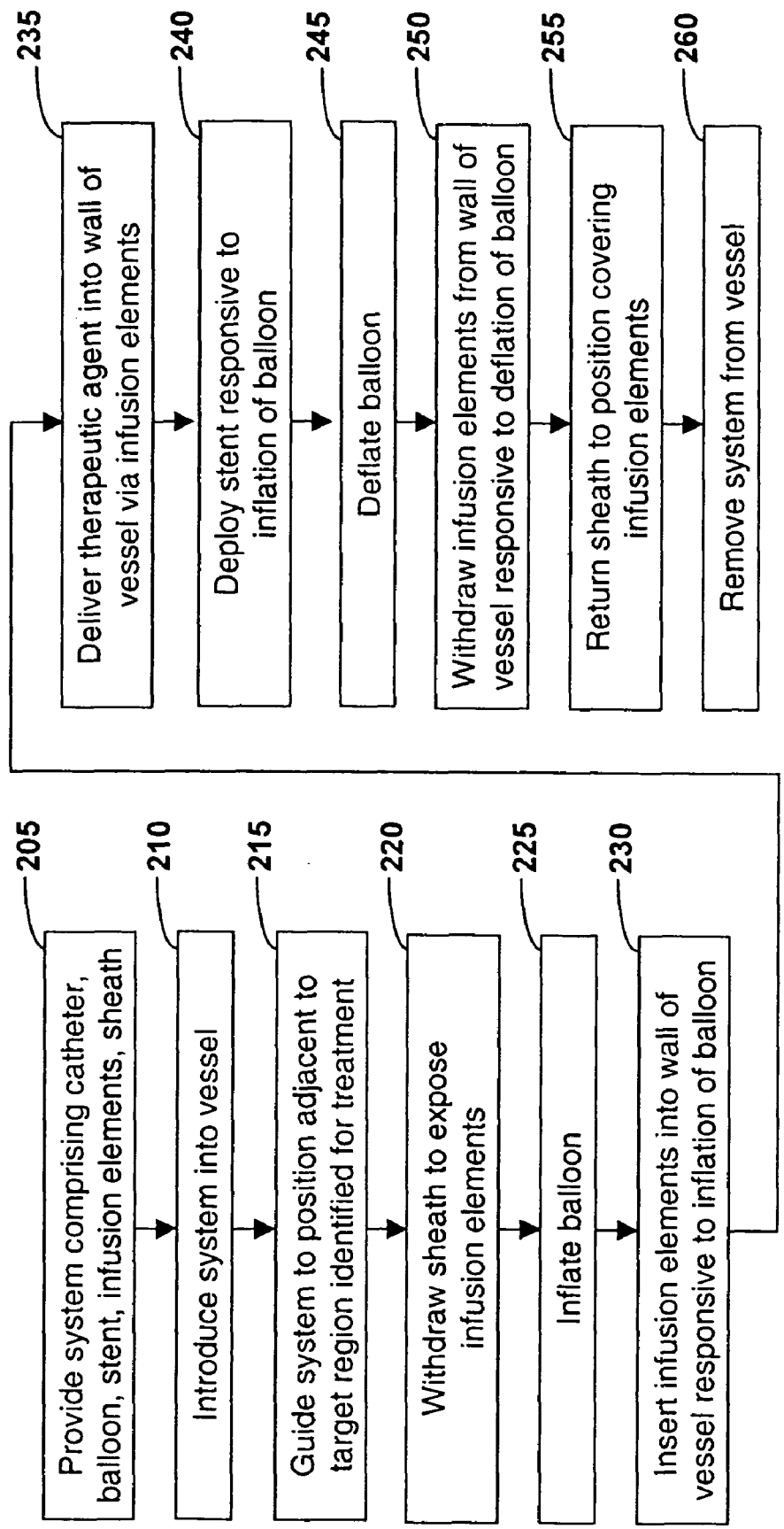
FIG. 2 is a flow diagram of one embodiment of a method of treating a vascular condition, in accordance with the present invention.

Another aspect of the present invention is a method of treating a vascular condition. FIG. 2 shows a flow diagram of one embodiment of the method in accordance with the present invention.

A system is provided comprising a catheter having an inflation lumen and at least one therapeutic agent delivery lumen, a balloon disposed on the catheter, a stent disposed on the balloon, a plurality of therapeutic agent infusion elements positioned adjacent to proximal and distal ends of the stent, and a sheath removably covering the infusion elements (Block 205). The balloon comprises proximal and distal end portions and a center portion. The stent is mounted on the center portion of the balloon. The infusion elements are mounted on one or more therapeutic agent delivery manifolds, the manifold or manifolds mounted on the proximal and distal end portions of the balloon.

The system is introduced into a vessel containing a target region identified for treatment (Block 210) and guided to a position adjacent to the target region (Block 215). Once the system is in position, the sheath is withdrawn to expose the infusion elements (Block 220), and the balloon is inflated (Block 225). In an alternative embodiment, either or both of the manifold and the balloon may be folded such that the infusion elements are held within the folds of the uninflated balloon and/or manifold during delivery of the system to the target region. The vessel is shielded from the infusion elements by the balloon and/or manifold, eliminating the need for a sheath.

The proximal and distal end portions of the balloon inflate at one inflation pressure, whereas the center portion of the balloon inflates at a second, greater inflation pressure. When the first inflation pressure is provided to the balloon via an inflation lumen within the catheter, the proximal and distal portions of the balloon inflate, inserting the infusion elements positioned on these portions of the balloon into a wall of the target region of the vessel (Block 230). In the present embodiment, the infusion elements are hollow, stainless steel needles that pierce the wall of the vessel in response to inflation of the balloon.

One or more therapeutic agents are delivered into the wall of the target region of the vessel via the infusion elements (Block 235). The therapeutic agents are carried by the therapeutic agent delivery lumen within the catheter and supplied to the infusion elements via the manifold or manifolds on which the infusion elements are mounted.

A second, greater inflation pressure is then provided to the balloon, inflating the center portion of the balloon and deploying the stent (Block 240). In an alternative embodiment, a single inflation pressure may inflate all portions of the balloon, delivering the stent at approximately the same time the infusion elements are thrust into the wall of the vessel.

Once one or more therapeutic agents have been delivered to the wall of the vessel and the stent has been deployed, the balloon is deflated (Block 245). The infusion elements are withdrawn from the wall of the vessel in response to deflation of the balloon (Block 250). The sheath is returned to a position covering the infusion elements (Block 255), and the system is removed from the vessel (Block 220). In an alternative embodiment, the need for a sheath may be eliminated by moving the infusion elements back inside the folds of the deflated balloon and/or manifold in response to deflation of the balloon, thereby enclosing the infusion elements and preventing trauma to the vessel during removal of the catheter from the vessel.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A system for treating a vascular condition, comprising:
a catheter having an inflation lumen and a therapeutic agent delivery lumen;
an inflatable balloon disposed on the catheter and in fluid communication with the inflation lumen, the balloon comprising a proximal end portion, a distal end portion, and a center portion;
a stent detachably disposed on the balloon;
an annular expandable manifold disposed on one of the proximal end portion and the distal end portion of the balloon adjacent to the stent and extending around the entire circumference of the one of the proximal end portion and the distal end portion of the balloon, the expandable manifold having an axial length less than the axial length of the one of the proximal end portion and the distal end portion of the balloon, the expandable manifold being in fluid communication with the therapeutic agent delivery lumen; and
a plurality of infusion elements positioned on an outer circumference of the expandable manifold and in fluid communication with the expandable manifold,
wherein the plurality of infusion elements includes an axially oriented delivery position and a radially oriented infusion position, the plurality of infusion elements being configured to move from the axially oriented delivery position to the radially oriented infusion position upon inflation of the one of the proximal end portion and the distal end portion.

2. The system of claim 1 further comprising:
at least one sheath removably positioned over the infusion elements.

3. The system of claim 2 wherein the sheath is tapered.

4. The system of claim 1 wherein the balloon center portion has an inflation diameter greater than the inflation diameter of the proximal end portion and greater than the inflation diameter of the distal end portion.

5. The system of claim 4 wherein the stent is disposed on the center portion of the balloon.

6. The system of claim 4 wherein the proximal and distal end portions of the balloon inflate at a first inflation pressure, and wherein the center portion of the balloon inflates at a second inflation pressure that is greater than the first inflation pressure.

7. The system of claim 1 wherein the infusion elements are hollow needles.

8. The system of claim 1 further comprising:
a therapeutic coating disposed on at least a portion of the stent.

9. The system of claim 8 wherein the therapeutic coating includes a therapeutic agent selected from a group consisting of an antineoplastic agent, an antiproliferative agent, an antibiotic, an antithrombogenic agent, an anticoagulant, an antiplatelet agent, an anti-inflammatory agent, and combinations thereof.

10. The system of claim 1 wherein the annular expandable manifold disposed on the one of the proximal end portion and the distal end portion of the balloon is a first expandable manifold, and the system further comprises a second expandable manifold disposed on the other of the proximal end portion and the distal end portion of the balloon adjacent to the stent, the second expandable manifold being annular.

11. The system of claim 10 further comprising a linking section between the first expandable manifold and the second expandable manifold, and wherein at least one of the plurality of infusion elements is mounted on the first expandable manifold and at least one of the plurality of infusion elements is mounted on the second expandable manifold.

12. The system of claim 11 wherein the first expandable manifold extends around the entire circumference of the proximal end portion of the balloon, the second expandable manifold extends around the entire circumference of the distal end portion of the balloon, and the linking section extends longitudinally across the center portion of the balloon.

13. The system of claim 12 wherein the first expandable manifold is in fluid communication with the therapeutic agent delivery lumen, and the second expandable manifold is in fluid communication with the first expandable manifold via the linking section.

14. The system of claim 12 wherein the second expandable manifold is in fluid communication with therapeutic agent delivery lumen, and the first expandable manifold is in fluid communication with the second expandable manifold via the linking section.

15. The system of claim 10 wherein the first expandable manifold and at least one of the plurality of infusion elements are disposed on the proximal end portion of the balloon and in fluid communication with the therapeutic agent lumen, and wherein the second expandable manifold and at least one of the plurality of infusion elements are disposed on the distal end portion of the balloon and in fluid communication with the therapeutic agent lumen.

16. The system of claim 15 wherein the first expandable manifold extends around the entire circumference of the proximal end portion of the balloon and wherein the second expandable manifold extends around the entire circumference of the distal end portion of the balloon.

17. The system of claim 10 wherein:
the first expandable manifold is separated from the second expandable manifold by an axial length of the center portion of the balloon.

18. The system of claim 17 further comprising a manifold linking section in fluid communication between the first expandable manifold and the second expandable manifold.

* * * * *